US012104208B2

(12) United States Patent
Molina et al.

(10) Patent No.: US 12,104,208 B2
(45) Date of Patent: Oct. 1, 2024

(54) GENETIC IDENTIFICATION OF *PISCIRICKETTSIA SALMONIS* RESISTANT SALMONIDS

(71) Applicant: BLUE GENOMICS CHILE SPA, Puerto Varas (CL)

(72) Inventors: Daniela Cichero Molina, Puerto Varas (CL); Jorgen Odegard, Vestfold (NO); Sven Korsvoll, Kyrksaeterora (NO)

(73) Assignee: BLUE GENOMICS CHILE SPA, Puerto Varas (CL)

(*) Notice: Subject to any disclaimer, the term of this patent is extended or adjusted under 35 U.S.C. 154(b) by 610 days.

(21) Appl. No.: 16/617,980

(22) PCT Filed: May 31, 2018

(86) PCT No.: PCT/GB2018/051494
§ 371 (c)(1),
(2) Date: Nov. 27, 2019

(87) PCT Pub. No.: WO2018/220385
PCT Pub. Date: Dec. 6, 2018

(65) Prior Publication Data
US 2020/0190582 A1    Jun. 18, 2020

(30) Foreign Application Priority Data
May 31, 2017    (GB) .................... 1708617

(51) Int. Cl.
C12Q 1/68    (2018.01)
C12P 19/34    (2006.01)
C12Q 1/6876    (2018.01)
(52) U.S. Cl.
CPC ..... *C12Q 1/6876* (2013.01); *C12Q 2600/124* (2013.01); *C12Q 2600/156* (2013.01)
(58) Field of Classification Search
CPC ............. C12Q 1/6883; C12Q 1/6876; C12Q 2600/124; C12Q 2600/156
See application file for complete search history.

(56) References Cited

U.S. PATENT DOCUMENTS 6,673,352 B1    1/2004    Donahoe et al.

FOREIGN PATENT DOCUMENTS

CA    2864258 A1    3/2015
WO    01/77384 A2    12/2001

OTHER PUBLICATIONS

Moen et al. BMC Genomic 2009. 10:638, fourteen pages (Year: 2009).*
Hilary Starks, et al. "Discovery and characterization of single nucleotide polymorphisms in coho salmon, Oncorhynchus kisutch" May 2015Molecular Ecology Resources 16(1) (Year: 2015).*
NIH, NLM BioProject Accession PRJNA378663, printed from https://www.ncbi.nlm.nih.gov/bioproject/378663. (Year: 2017).*
Jin-Hyoung Kim, et al. "Multi-tissue transcriptome profiles for coho salmon (*Oncorhynchus kisutch*), a species undergoing rediploidization following whole-genome duplication" Marine Genomics, Feb. 2016;25:33-3 (Epub Nov. 21, 2015) (Year: 2015).*
NCBI Reference Sequence: NC_034194.1 "Oncorhynchus kisutch isolate 150728-3 linkage group LG21, Okis_V1, whole genome shotgun sequence" (Mar. 14, 2017) from https://www.ncbi.nlm.nih.gov/nuccore/NC_034194.1?report=GenBank (Year: 2017).*
Examination Report for EP 18 730 071.0, dated Dec. 4, 2020.
International Search Report and Written Opinion for corresponding Application No. PCT/GB2018/051494 (mailed Jul. 26, 2018).
International Preliminary Report on Patentability for corresponding Application No. PCT/GB2018/051494 (mailed May 8, 2019).
Moen et al., "Confirmation and Fine-Mapping of a Major QTL for Resistance to Infectious Pancreatic Necrosis in Atlantic Salmon (*Salmo salar*): Population-Level Associations between Markers and Trait," BMC Genom. Biomed Central 10(1):368 (2009).
Odegard et al., "Genomic Prediction in an Admixed Population fo Atlantic Salmon (*Salmo salar*)," Front. Gen. 5(21):1-8.
Bangera et al., "Genomic Predictions can Accelerate Selection for Resistance Against Piscirickettsia salmonis in Atlantic Salmon (*Salmo salar*)," BMC Genomic. 18(121):1-12 (2017).
Odegard et al, "Methodology for Genetic Evaluation of Disease Resistance in Aquaculture Species: Challenges and Future Prospects," Aquacult. Res. 42:103-114 (2011).
Gomez et al., "MHC Mediated Resistance to Piscirickettsia salmonis in Salmonids Farmed in Chile," Aquacult. 318(1-2):15-19 (2011) (abstract only).

* cited by examiner

*Primary Examiner* — Stephen T Kapushoc
(74) *Attorney, Agent, or Firm* — Troutman Pepper Hamilton Sanders LLP (Rochester)

(57) ABSTRACT

The invention relates to methods of predicting resistance to *Piscirickettsia salmonis* infection in a salmonid, the method comprising determining in the salmonid the alleles present at one or more DNA polymorphism within a QTL, and predicting the ability of the salmonid to be resistant to *Piscirickettsia salmonis* infection based on the determination of the alleles, wherein the QTL is: —(a) located in linkage group 21 (GenBank ID NC 034194.1) within the coho salmon genome, or in the chromosome of coho salmon that corresponds to that linkage group, when the salmonid is a coho salmon, or; (b) a QTL that is located in a linkage group that corresponds to linkage group 21 within the coho salmon genome, or in the chromosome of a salmonid that corresponds to that linkage group, when the salmonid is not a coho salmon. The invention further relates to probes and arrays useful in such method and related methods.

3 Claims, 2 Drawing Sheets

Specification includes a Sequence Listing.

SEQUENCE LISTING

```
<160> NUMBER OF SEQ ID NOS: 48

<210> SEQ ID NO 1
<211> LENGTH: 201
<212> TYPE: DNA
<213> ORGANISM: Atlantic salmon

<400> SEQUENCE: 1
atcattcaga atatatcctc aaacccagat atgtcaaacc atcaacactt tcaagcattg      60
ttccattact tgcatggatt ttgaaatggc cagctgtgga rtttattctt ttctgtgtac     120
atatccatgc aatgttgtct taatgtgtgt gtgtgtatat atatcagagc gaggagaaga    180
cccgtattaa ctcatccttg g                                              201

<210> SEQ ID NO 2
<211> LENGTH: 201
<212> TYPE: DNA
<213> ORGANISM: Atlantic salmon

<400> SEQUENCE: 2
aatgctttat ttttactttg caatatgcag tattcagtcc actgagagag gtacaggaca     60
taacaatagc ccaaaacaaa atgaacaaga ttgagttttt kggccttcta caatggctga    120
acctgtcaca caatcttata ggggaaatct attcttacac atttgaaaat ctacccagta    180
ttttagaact agacttatct t                                              201

<210> SEQ ID NO 3
<211> LENGTH: 201
<212> TYPE: DNA
<213> ORGANISM: Atlantic salmon

<400> SEQUENCE: 3
gtaattagaa atctgtatgc cgtgctgtag tgagtcatac tgcctgcaga gcccggtcta     60
atgtatatgt ttgctctgta gcagaaggtt tggccaggat mttggaccac cagggaaacc    120
tgttagaagg ggggatggat ggcaggagcc agaagagcaa ataaaacaca ggattcgtga    180
atgaatggaa ttcgtaaatg a                                              201

<210> SEQ ID NO 4
<211> LENGTH: 201
<212> TYPE: DNA
<213> ORGANISM: Atlantic salmon

<400> SEQUENCE: 4
tggtggttct ggaggctgct gcctttattt tatgagggat ctgaggagtc tcctctacat     60
gaggcctcag gtgatccatg cttattttag ggaagataac mcccttgtca tcttccacgt    120
ccacactttt gcttttgaga cctcgaatcg tacattggcc gagatagttg tgatctagtt    180
```
cgccccsctt cctctgctgg t                                                        201

<210> SEQ ID NO 5
<211> LENGTH: 201
<212> TYPE: DNA
<213> ORGANISM: Atlantic salmon

<400> SEQUENCE: 5
tctcttgtga cacctgacta gagtaaggct gtgtacccag cacacaaata aagtcttttc    60
attatcagat tgggacagaa actgtgaact atggatattt maaagagaca gttaaatgtg   120
aattcgctat agccaaggat gtctcatctg aagcggatac tcttaagact gatacagcca   180
acaaattaat ttatggactg t                                              201

<210> SEQ ID NO 6
<211> LENGTH: 201
<212> TYPE: DNA
<213> ORGANISM: Atlantic salmon

<400> SEQUENCE: 6
gacctcctct ggtttctcta gaaccgccca tgaatgctgc ttatcctctg gtccacattc    60
ctctgtgatg tcattataaa atcccacaaa cttcttgttg rtggaatctt cgaggaaaac   120
gtcattgaca tcatctccag acctgatatg ctctaaaacc ctgttgacag agttctgtgc   180
gtcggcccag gaatgtagcc t                                              201

<210> SEQ ID NO 7
<211> LENGTH: 201
<212> TYPE: DNA
<213> ORGANISM: Atlantic salmon

<400> SEQUENCE: 7
tcgctcacgt tctccaagtt gatgacgttc cagatggctt tgacgtagtc gggtcgaacg    60
ttcttgtact ggcgatagta gatgttccca tatatcaata mccagcagag ggaccaaacc   120
tggggagaaa aaaatgactt taagtaaaat aatgatgcag cttcaaagta tttgaacagg   180
ccagacatcc atatggttat t                                              201

<210> SEQ ID NO 8
<211> LENGTH: 201
<212> TYPE: DNA
<213> ORGANISM: Atlantic salmon

<400> SEQUENCE: 8
aactgaacag gatcagttgg atctgacaaa aagccattca actttgatag atggcaaagg    60
agtatttcag tgtctacaaa ctgtaaggtc tgaagaacac yggcttaggg gaagcccttt   120
cagcccggta tctgtctcta ctgatccaaa tgaaatggag ttgaccaggt gcccaacttt   180
tgccattgac ttcaaagcca t                                              201

<210> SEQ ID NO 9
<211> LENGTH: 201
<212> TYPE: DNA
<213> ORGANISM: Atlantic salmon

<400> SEQUENCE: 9
aagatctctg caaaaacggc acaattaatc acatatttct tgagttactt ttgtgtatat    60
actggctaca gcatctcaaa atagacagac agtactattg ycgctttttt ctcattttgt   120
cacgacttcg gccgaagttg gctcccctgc ctgttcgggc ggtgctcggc agtcgtcgtc   180
accgtcctac tagccgccgt c                                               201

<210> SEQ ID NO 10
<211> LENGTH: 201
<212> TYPE: DNA
<213> ORGANISM: Atlantic salmon

<400> SEQUENCE: 10
tcagaggtta gcttatcatt actttccctt ggtgccttgc ggttacatcg ttttgtaccg     60
tgttcagtca tcaataatac agtttctaat ccggttacag mcaggagagc cttctgcatt    120
ataatagcgt acagtaatct ccatccattg acactgtagc ccatcctcat acctgtcaat    180
gatgagccat tgggttctga g                                              201

<210> SEQ ID NO 11
<211> LENGTH: 201
<212> TYPE: DNA
<213> ORGANISM: Atlantic salmon

<400> SEQUENCE: 11
gttgattcaa cctcaacaca tatttggggt tgaaatgaga tggaaacaat gttgattcac     60
ccagctgtta cccagtggct ggttgtttag catgataggc rggttcagag agaacttgtt    120
tgttcttggt cagcaactac gccatccaga aaggaacttc cttccttgat caatcgaaga    180
catggaggga ggcttatata a                                              201

<210> SEQ ID NO 12
<211> LENGTH: 201
<212> TYPE: DNA
<213> ORGANISM: Atlantic salmon

<400> SEQUENCE: 12
taaataaaac atgtatatgc tttacaattt actacaaatc cagaaagtat ggtgtcatag     60
tattttccat gcatacatta tgctgctgtc atgaacaatt matctaatta aacatgagtt    120
aatatttgtt gtagtaaaaa agtatatctc ccacagatta aaacatcatt tcctccattt    180
tgtccggcgc tggtagacgt c                                              201

<210> SEQ ID NO 13
<211> LENGTH: 201
<212> TYPE: DNA
<213> ORGANISM: Atlantic salmon

<400> SEQUENCE: 13
ttagatctaa agtcgaccac acttaccgct gtgtccctat gtaggctgca gtgacatgta     60
ttcatggatg ccaaggaaag ccatgcttcc acccaaaaat kacgaataaa aatgtaacaa    120
atttaaaaac atatctttcg tctcactgcg tttcataatt tcccttcaat tcgcaagagg    180
ctgaatgtat ctcaccagtg a                                              201

<210> SEQ ID NO 14
<211> LENGTH: 201
<212> TYPE: DNA
<213> ORGANISM: Atlantic salmon

<400> SEQUENCE: 14
gacgtgcaga tccctggacg atggcgtaca gtaagaacac caagaggaag tttttcttca     60
acaagatgac taaacagtcc acttacgacc tgccagccaa ytctgtggcc ccgttccagt    120

-continued

| | |
|---|---|
| gcgtaccact atgcaccggt ctcaaatctg tgtggtagac taggatatgt gcgacaagga | 180 |
| attgtctgca tgtttttgca t | 201 |

<210> SEQ ID NO 15
<211> LENGTH: 201
<212> TYPE: DNA
<213> ORGANISM: Atlantic salmon

<400> SEQUENCE: 15

| | |
|---|---|
| tagatgcctc ctgcagagtc aactacacat caagattgag aagtgggagt tccatgtatc | 60 |
| ccaagtctct ttcctgggac acatgatctc taccgccagc mttaaaatgg accctgttaa | 120 |
| ggttagggcg gtcactgact ggccccgtcc cgcctcactt aaacaagtcc agcgggtcct | 180 |
| cgggtttgcc aattttttaca g | 201 |

<210> SEQ ID NO 16
<211> LENGTH: 201
<212> TYPE: DNA
<213> ORGANISM: Atlantic salmon

<400> SEQUENCE: 16

| | |
|---|---|
| aggcctaatg gtggccattg gctggggcta cgctatccct cccaatgcca cagcattcca | 60 |
| cagctacggc ctctgcaaca catcacactt ctcagacgta ygttcagtgc tctttgacac | 120 |
| tagattgaag aaggatggtt gattttgatg acattgtaga gcagattgtt gtcaaaaaag | 180 |
| gaaagcgcca gcttactctt t | 201 |

<210> SEQ ID NO 17
<211> LENGTH: 201
<212> TYPE: DNA
<213> ORGANISM: Atlantic salmon

<400> SEQUENCE: 17

| | |
|---|---|
| gctagttgtt tttagagaac cagctgtgct tatggcttaa cacaatttag tttgccgtgg | 60 |
| aaaatatcaa cgccatgaca acattctcat ggccaaatca kggaagcagt aatatatcac | 120 |
| actagcaaat accagcgcca taccgtgacc aaataccata ccgtgatgga gataattatg | 180 |
| aaactagcta gcttgttaac t | 201 |

<210> SEQ ID NO 18
<211> LENGTH: 201
<212> TYPE: DNA
<213> ORGANISM: Atlantic salmon

<400> SEQUENCE: 18

| | |
|---|---|
| gtaagcattt catggtaaag tctacacccg ttgtatttgg cgcatgtgac aaatattttt | 60 |
| gggggtattt tattttattc tcatgtatca cgcttgtgac rtccctggcc ttttgcagca | 120 |
| ctgatgcttc tgtaatgaga tgctatatga gacatgccaa agcacccaca cactgtgaca | 180 |
| aagagtaaaa caacatgaga c | 201 |

<210> SEQ ID NO 19
<211> LENGTH: 71
<212> TYPE: DNA
<213> ORGANISM: Atlantic salmon

<400> SEQUENCE: 19

| | |
|---|---|
| tttatttttc accgtacaca agtcttcaaa tgggtmattt ccccatgta tattcattag | 60 |
| tctgcaggtg t | 71 |

<210> SEQ ID NO 20
<211> LENGTH: 201
<212> TYPE: DNA
<213> ORGANISM: Atlantic salmon

<400> SEQUENCE: 20

```
atcattcaga atatatcctc aaacccagat atgtcaaacc atcaacactt tcaagcattg      60
ttccattact tgcatggatt ttgaaatggc cagctgtgga gtttattctt ttctgtgtac     120
atatccatgc aatgttgtct taatgtgtgt gtgtgtatat atatcagagc gaggagaaga    180
cccgtattaa ctcatccttg g                                              201
```

<210> SEQ ID NO 21
<211> LENGTH: 201
<212> TYPE: DNA
<213> ORGANISM: Atlantic salmon

<400> SEQUENCE: 21

```
aatgctttat ttttactttg caatatgcag tattcagtcc actgagagag gtacaggaca      60
taacaatagc ccaaaacaaa atgaacaaga ttgagttttt gggccttcta caatggctga    120
acctgtcaca caatcttata ggggaaatct attcttacac atttgaaaat ctacccagta    180
ttttagaact agacttatct t                                              201
```

<210> SEQ ID NO 22
<211> LENGTH: 201
<212> TYPE: DNA
<213> ORGANISM: Atlantic salmon

<400> SEQUENCE: 22

```
gtaattagaa atctgtatgc cgtgctgtag tgagtcatac tgcctgcaga gcccggtcta      60
atgtatatgt ttgctctgta gcagaaggtt tggccaggat attggaccac cagggaaacc    120
tgttagaagg ggggatggat ggcaggagcc agaagagcaa ataaaacaca ggattcgtga    180
atgaatggaa ttcgtaaatg a                                              201
```

<210> SEQ ID NO 23
<211> LENGTH: 201
<212> TYPE: DNA
<213> ORGANISM: Atlantic salmon

<400> SEQUENCE: 23

```
tggtggttct ggaggctgct gcctttattt tatgagggat ctgaggagtc tcctctacat      60
gaggcctcag gtgatccatg cttattttag ggaagataac accttgtca tcttccacgt     120
ccacactttt gcttttgaga cctcgaatcg tacattggcc gagatagttg tgatctagtt    180
cgcccccttt cctctgctgg t                                              201
```

<210> SEQ ID NO 24
<211> LENGTH: 201
<212> TYPE: DNA
<213> ORGANISM: Atlantic salmon

<400> SEQUENCE: 24

```
tctcttgtga cacctgacta gagtaaggct gtgtacccag cacacaaata aagtctttc       60
attatcagat tgggacagaa actgtgaact atggatattt caagagaca gttaaatgtg    120
aattcgctat agccaaggat gtctcatctg aagcggatac tcttaagact gatacagcca    180
```
acaaattaat ttatggactg t                                           201

<210> SEQ ID NO 25
<211> LENGTH: 201
<212> TYPE: DNA
<213> ORGANISM: Atlantic salmon

<400> SEQUENCE: 25
gacctcctct ggtttctcta gaaccgccca tgaatgctgc ttatcctctg gtccacattc    60
ctctgtgatg tcattataaa atcccacaaa cttcttgttg gtggaatctt cgaggaaaac   120
gtcattgaca tcatctccag acctgatatg ctctaaaacc ctgttgacag agttctgtgc   180
gtcggcccag gaatgtagcc t                                           201

<210> SEQ ID NO 26
<211> LENGTH: 201
<212> TYPE: DNA
<213> ORGANISM: Atlantic salmon

<400> SEQUENCE: 26
tcgctcacgt tctccaagtt gatgacgttc cagatggctt tgacgtagtc gggtcgaacg    60
ttcttgtact ggcgatagta gatgttccca tatatcaata accagcagag ggaccaaacc   120
tggggagaaa aaaatgactt taagtaaaat aatgatgcag cttcaaagta tttgaacagg   180
ccagacatcc atatggttat t                                           201

<210> SEQ ID NO 27
<211> LENGTH: 201
<212> TYPE: DNA
<213> ORGANISM: Atlantic salmon

<400> SEQUENCE: 27
aactgaacag gatcagttgg atctgacaaa aagccattca actttgatag atggcaaagg    60
agtatttcag tgtctacaaa ctgtaaggtc tgaagaacac cggcttaggg gaagcccttt   120
cagcccggta tctgtctcta ctgatccaaa tgaaatggag ttgaccaggt gcccaacttt   180
tgccattgac ttcaaagcca t                                           201

<210> SEQ ID NO 28
<211> LENGTH: 201
<212> TYPE: DNA
<213> ORGANISM: Atlantic salmon

<400> SEQUENCE: 28
aagatctctg caaaaacggc acaattaatc acatatttct tgagttactt ttgtgtatat    60
actggctaca gcatctcaaa atagacagac agtactattg tcgcttttt ctcatttgt   120 cacgacttcg gccgaagttg gctcccctgc ctgttcgggc ggtgctcggc agtcgtcgtc   180
accgtcctac tagccgccgt c                                           201

<210> SEQ ID NO 29
<211> LENGTH: 201
<212> TYPE: DNA
<213> ORGANISM: Atlantic salmon

<400> SEQUENCE: 29
tcagaggtta gcttatcatt actttccctt ggtgccttgc ggttacatcg ttttgtaccg    60
tgttcagtca tcaataatac agtttctaat ccggttacag acaggagagc cttctgcatt   120
ataatagcgt acagtaatct ccatccattg acactgtagc ccatcctcat acctgtcaat   180

```
gatgagccat tgggttctga g                                              201
```

<210> SEQ ID NO 30
<211> LENGTH: 201
<212> TYPE: DNA
<213> ORGANISM: Atlantic salmon

<400> SEQUENCE: 30

```
gttgattcaa cctcaacaca tatttggggt tgaaatgaga tggaaacaat gttgattcac     60
ccagctgtta cccagtggct ggttgtttag catgataggc gggttcagag agaacttgtt    120
tgttcttggt cagcaactac gccatccaga aaggaacttc cttccttgat caatcgaaga    180
catggaggga ggcttatata a                                              201
```

<210> SEQ ID NO 31
<211> LENGTH: 201
<212> TYPE: DNA
<213> ORGANISM: Atlantic salmon

<400> SEQUENCE: 31

```
taaataaaac atgtatatgc tttacaattt actacaaatc cagaaagtat ggtgtcatag     60
tattttccat gcatacatta tgctgctgtc atgaacaatt aatctaatta aacatgagtt    120
aatatttgtt gtagtaaaaa agtatatctc ccacagatta aaacatcatt tcctccattt    180
tgtccggcgc tggtagacgt c                                              201
```

<210> SEQ ID NO 32
<211> LENGTH: 201
<212> TYPE: DNA
<213> ORGANISM: Atlantic salmon

<400> SEQUENCE: 32

```
ttagatctaa agtcgaccac acttaccgct gtgtccctat gtaggctgca gtgacatgta     60
ttcatggatg ccaaggaaag ccatgcttcc acccaaaaat tacgaataaa aatgtaacaa    120
atttaaaaac atatctttcg tctcactgcg tttcataatt tcccttcaat tcgcaagagg    180
ctgaatgtat ctcaccagtg a                                              201
```

<210> SEQ ID NO 33
<211> LENGTH: 71
<212> TYPE: DNA
<213> ORGANISM: Atlantic salmon

<400> SEQUENCE: 33

```
tttattttt accgtacaca agtcttcaaa tgggtcattt cccccatgta tattcattag     60
tctgcaggtg t                                                          71
```

<210> SEQ ID NO 34
<211> LENGTH: 201
<212> TYPE: DNA
<213> ORGANISM: Atlantic salmon

<400> SEQUENCE: 34

```
atcattcaga atatatcctc aaacccagat atgtcaaacc atcaacactt tcaagcattg     60
ttccattact tgcatggatt ttgaaatggc cagctgtgga atttattctt ttctgtgtac    120
atatccatgc aatgttgtct taatgtgtgt gtgtgtatat atatcagagc gaggagaaga    180
cccgtattaa ctcatccttg g                                              201
```

<210> SEQ ID NO 35
<211> LENGTH: 201
<212> TYPE: DNA
<213> ORGANISM: Atlantic salmon

<400> SEQUENCE: 35
aatgctttat ttttactttg caatatgcag tattcagtcc actgagagag gtacaggaca      60
taacaatagc ccaaaacaaa atgaacaaga ttgagttttt tggccttcta caatggctga     120
acctgtcaca caatcttata ggggaaatct attcttacac atttgaaaat ctacccagta     180
ttttagaact agacttatct t                                                201

<210> SEQ ID NO 36
<211> LENGTH: 201
<212> TYPE: DNA
<213> ORGANISM: Atlantic salmon

<400> SEQUENCE: 36
gtaattagaa atctgtatgc cgtgctgtag tgagtcatac tgcctgcaga gcccggtcta      60
atgtatatgt ttgctctgta gcagaaggtt tggccaggat cttggaccac cagggaaacc     120
tgttagaagg ggggatggat ggcagagcc agaagagcaa ataaaacaca ggattcgtga     180
atgaatggaa ttcgtaaatg a                                                201

<210> SEQ ID NO 37
<211> LENGTH: 201
<212> TYPE: DNA
<213> ORGANISM: Atlantic salmon

<400> SEQUENCE: 37
tggtggttct ggaggctgct gcctttattt tatgagggat ctgaggagtc tcctctacat      60
gaggcctcag gtgatccatg cttattttag ggaagataac ccccttgtca tcttccacgt     120
ccacactttt gcttttgaga cctcgaatcg tacattggcc gagatagttg tgatctagtt     180
cgcccccttt cctctgctgg t                                                201

<210> SEQ ID NO 38
<211> LENGTH: 201
<212> TYPE: DNA
<213> ORGANISM: Atlantic salmon

<400> SEQUENCE: 38
tctcttgtga cacctgacta gagtaaggct gtgtacccag cacacaaata aagtcttttc      60
attatcagat tgggacagaa actgtgaact atggatattt aaaagagaca gttaaatgtg     120
aattcgctat agccaaggat gtctcatctg aagcggatac tcttaagact gatacagcca     180
acaaattaat ttatggactg t                                                201

<210> SEQ ID NO 39
<211> LENGTH: 201
<212> TYPE: DNA
<213> ORGANISM: Atlantic salmon

<400> SEQUENCE: 39
gacctcctct ggtttctcta gaaccgccca tgaatgctgc ttatcctctg gtccacattc      60
ctctgtgatg tcattataaa atcccacaaa cttcttgttg atggaatctt cgaggaaaac     120
gtcattgaca tcatctccag acctgatatg ctctaaaacc ctgttgacag agttctgtgc     180
gtcggcccag gaatgtagcc t                                                201

<210> SEQ ID NO 40
<211> LENGTH: 201
<212> TYPE: DNA
<213> ORGANISM: Atlantic salmon

<400> SEQUENCE: 40

```
tcgctcacgt tctccaagtt gatgacgttc cagatggctt tgacgtagtc gggtcgaacg      60
ttcttgtact ggcgatagta gatgttccca tatatcaata cccagcagag ggaccaaacc     120
tggggagaaa aaatgactt taagtaaaat aatgatgcag cttcaaagta tttgaacagg      180
ccagacatcc atatggttat t                                               201
```

<210> SEQ ID NO 41
<211> LENGTH: 201
<212> TYPE: DNA
<213> ORGANISM: Atlantic salmon

<400> SEQUENCE: 41

```
aactgaacag gatcagttgg atctgacaaa aagccattca actttgatag atggcaaagg      60
agtatttcag tgtctacaaa ctgtaaggtc tgaagaacac tggcttaggg gaagcccttt     120
cagcccggta tctgtctcta ctgatccaaa tgaaatggag ttgaccaggt gcccaacttt     180
tgccattgac ttcaaagcca t                                               201
```

<210> SEQ ID NO 42
<211> LENGTH: 201
<212> TYPE: DNA
<213> ORGANISM: Atlantic salmon

<400> SEQUENCE: 42

```
aagatctctg caaaaacggc acaattaatc acatatttct tgagttactt ttgtgtatat      60
actggctaca gcatctcaaa atagacagac agtactattg ccgcttttttt ctcattttgt    120
cacgacttcg gccgaagttg gctcccctgc ctgttcgggc ggtgctcggc agtcgtcgtc     180
accgtcctac tagccgccgt c                                               201
```

<210> SEQ ID NO 43
<211> LENGTH: 201
<212> TYPE: DNA
<213> ORGANISM: Atlantic salmon

<400> SEQUENCE: 43

```
tcagaggtta gcttatcatt actttcccctt ggtgccttgc ggttacatcg ttttgtaccg     60
tgttcagtca tcaataatac agtttctaat ccggttacag ccaggagagc cttctgcatt    120
ataatagcgt acagtaatct ccatccattg acactgtagc ccatcctcat acctgtcaat    180
gatgagccat tgggttctga g                                               201
```

<210> SEQ ID NO 44
<211> LENGTH: 201
<212> TYPE: DNA
<213> ORGANISM: Atlantic salmon

<400> SEQUENCE: 44

```
gttgattcaa cctcaacaca tatttggggt tgaaatgaga tggaaacaat gttgattcac      60
ccagctgtta cccagtggct ggttgtttag catgataggc aggttcagag agaacttgtt    120
tgttcttggt cagcaactac gccatccaga aaggaacttc cttccttgat caatcgaaga    180
```

```
catggaggga ggcttatata a                                              201

<210> SEQ ID NO 45
<211> LENGTH: 201
<212> TYPE: DNA
<213> ORGANISM: Atlantic salmon

<400> SEQUENCE: 45
taaataaaac atgtatatgc tttacaattt actacaaatc cagaaagtat ggtgtcatag     60
tattttccat gcatacatta tgctgctgtc atgaacaatt catctaatta aacatgagtt    120
aatatttgtt gtagtaaaaa agtatatctc ccacagatta aaacatcatt tcctccattt    180
tgtccggcgc tggtagacgt c                                              201

<210> SEQ ID NO 46
<211> LENGTH: 201
<212> TYPE: DNA
<213> ORGANISM: Atlantic salmon

<400> SEQUENCE: 46
ttagatctaa agtcgaccac acttaccgct gtgtccctat gtaggctgca gtgacatgta     60
ttcatggatg ccaaggaaag ccatgcttcc acccaaaaat gacgaataaa aatgtaacaa    120
atttaaaaac atatctttcg tctcactgcg tttcataatt tcccttcaat tcgcaagagg    180
ctgaatgtat ctcaccagtg a                                              201

<210> SEQ ID NO 47
<211> LENGTH: 71
<212> TYPE: DNA
<213> ORGANISM: Atlantic salmon

<400> SEQUENCE: 47 tttattttc accgtacaca agtcttcaaa tgggtaattt cccccatgta tattcattag     60
tctgcaggtg t                                                         71

<210> SEQ ID NO 48
<211> LENGTH: 71
<212> TYPE: DNA
<213> ORGANISM: Atlantic salmon

<400> SEQUENCE: 48
ctgtttatat ctatggccag ctagtcttaa tggttmgtga tggagtaaga caggttcaca     60
tctgggagga t                                                         71
```

GENETIC IDENTIFICATION OF *PISCIRICKETTSIA SALMONIS* RESISTANT SALMONIDS

This application is a national stage application under 35 U.S.C. § 371 of PCT Application No. PCT/GB2018/051494, filed May 31, 2018, which claims the priority benefit of Great Britain Patent Application Serial No. 1708617.4 filed May 31, 2017, which are hereby incorporated by reference in their entirety.

The present invention relates to methods for predicting the ability of salmonids to possess resistance to bacterial infection, in particular, predicting resistance to *Piscirickettsia salmonis*.

BACKGROUND

Salmon Rickettsial Syndrome (SRS, also known as piscirickettsiosis) is a bacterial disease that causes substantial economic losses and animal welfare problems within the aquaculture industry. For example, in the Chilean salmon farming industry, annual losses exceed US$150 million. *Piscirickettsia salmonis*, the causative agent of SRS, was first identified as a pathogenic agent in disease outbreaks among farmed Chilean Coho salmon in 1989, and since then, infectivity has been demonstrated in all cultured salmonid species, e.g. Atlantic salmon, rainbow trout, and coho salmon, from the south of Chile to the Northern Hemisphere. This pathogen has the ability to infect, replicate, and propagate in salmonid monocytes/macrophages, and produces a systemic infection characterized by the colonization of several organs, including the kidney, liver, spleen, intestine, brain, ovary, and gills. The pathogen has evolved over time, becoming more virulent with each outbreak and becoming refractory to treatments. Antibiotic use may inhibit the growth of the pathogen, but treatments have been unsuccessful in stopping disease outbreaks. Commercial vaccines have also not proven to be as efficient as needed.

In the absence of an efficient method to combat SRS, one approach that can be adopted is the selective breeding of fish with a propensity to increased resistance to *Piscirickettsia salmonis* infection. This methodology involves the selection of broodstock based on their perceived ability with respect to such resistance. In order to determine if any given fish possesses the required resistance, one can perform a challenge test on a population of fish. Such a test firstly involves the exposure of the fish to the bacteria; normally by injecting bacteria directly into some fish in the population, the fish receiving the injection then act as shedders and so infect the other fish in the population. After a period of 5-8 weeks, dead fish are analysed to confirm that their cause of death was bacterial infection, and the surviving fish registered as those with a propensity to resistance to infection. One highly significant limitation to this approach is that all tested fish must be sacrificed in order to avoid vertical transmission of the infection. As a consequence of this, all fish identified as having a propensity to resistance are lost as broodstock candidates. The typical solution to this problem is to establish broodstock from the siblings of the challenge-tested animals that demonstrate resistance, i.e., randomly chosen, untested, representatives of the best-performing sibling groups. This approach is often referred to as 'family selection'. Family selection relies on similarities between siblings. However, this predictive method has a limited potential as between-family genetic variation constitutes 50% of the total genetic variation in a population, while the remaining 50% genetic variation comes from within-family genetic variation.

Alternative methods of selecting bloodstock can be based on the detection of the presence or absence of a genetic marker that is associated with the desired phenotypic trait (ie Marker Assisted Selection, MAS). The present inventors are aware of another group that have tried to identify such a marker in coho salmon. Although the work of this other group has not been published in a peer reviewed article, it is understood that the most promising result from this relatively small study is a single nucleotide polymorphism (SNP) with only a moderate association to *Piscirickettsia salmonis* infection (having a significance level of $p=10^{-5}$ to $10^{-6}$). This SNP is thought to be located in a region that is homologous to Atlantic salmon chromosome Ssa03, containing the gene for Hem Oxygenase-2 (Barria et al. http://biorxiv.org/content/early/2017/04/04/124099; doi: https://doi.org/10.1101/124099).

There is therefore a need for markers for assaying animals' resistance to *Piscirickettsia salmonis* infection; particularly methodologies that allow the detection of individual's resistance to *Piscirickettsia salmonis* infection, whilst retaining the possibility of using the tested animal as broodstock.

There is therefore a need for alternative methodologies for predicting a salmonid's ability to be resistant to *Piscirickettsia salmonis* infection.

BRIEF SUMMARY OF THE DISCLOSURE

The inventors of the present invention have, following extensive experimentation, identified a new quantitative trait locus (QTL) in which DNA polymorphisms associated with resistance or non-resistance to *Piscirickettsia salmonis* infection are positioned. The inventors have found that one can predict a salmonid's ability to resist *Piscirickettsia salmonis* infection based on analysis of one or more of the polymorphisms found within the QTL region. The predictive power of these polymorphisms has been found to be greater than any disclosed to-date.

Accordingly, in a first aspect of the present invention, there is provided a method of predicting resistance to *Piscirickettsia salmonis* infection in a salmonid, the method comprising determining in the salmonid the alleles present at one or more DNA polymorphism within a QTL, and predicting the ability of the salmonid to be resistant to *Piscirickettsia salmonis* infection based on the determination of the alleles, wherein the QTL is: —
 (a) located in linkage group 21 within the coho salmon genome, or in the chromosome of coho salmon that corresponds to that linkage group, when the salmonid is a coho salmon, or;
 (b) a QTL that is located in a linkage group that corresponds to linkage group 21 within the coho salmon genome, or in the chromosome of a salmonid that corresponds to that linkage group, when the salmonid is not a coho salmon. For example, if the salmonid is a rainbow trout, the QTL would be located on rainbow trout chromosome 4. The QTL may be located in chromosome 6 of the genome of the Atlantic salmon, when the salmonid is an Atlantic salmon.

As would be understood by the person skilled in the art, a linkage group is a group of DNA markers that are co-inherited. When sufficient data is available, a linkage group is equivalent to a chromosome; the distinction between the two then refers only to the underlying source of information (the term 'linkage group' is used when genetic inheritance data is the only source of information). If insufficient genetic inheritance data is available, two or more linkage groups may correspond to one and the same chromosome due to insufficient inheritance data. Linkage group 21 is a linkage group acknowledged in the art as being found in the coho salmon genome. This linkage group may be defined by GenBbank accession No. NC_034194 (eg NCBI Reference Sequence NC_034194.1). This linkage group was put together through this process: 1) Next-generation sequencing was used in order to produce so-called scaffolds; contiguous sequences which are made on the basis of sequence information only (there will typically be tens- or hundreds of thousands of such scaffolds). 2) the scaffolds were ordered and oriented using inheritance patterns of DNA markers located within the scaffolds. The Inventors have found that the regions of the coho genome corresponding to NW_018086972.1 or NW_018107982.1 are linked to (i.e. on the same chromosome as) the region corresponding to NC_034194). Thus, the QTL of the present invention may be found within GenBank sequences NW_018086972.1 or NW_018107982.1 in coho salmon, or corresponding sequences in an alternative salmonid.

In light of the fact that *Piscirickettsia salmonis* is the causative agent for SRS, the methods of the present invention may be used to predict resistance to the development of SRS based on the determination of the alleles.

Although *Piscirickettsia salmonis* infection, and the resulting development of SRS, was first identified in coho salmon, this has since been found to be a general problem for salmonids. Additionally, the QTL identified by the present inventors in coho salmon is provided in a portion of the genome that is highly conserved across the salmonid species. The Inventors have found, for example, that there is a large degree of synteny between coho and rainbow trout, meaning that there is generally a close relationship between whole chromosomes (linkage groups) in coho and specific chromosomes or chromosome arms in rainbow trout. Consequently, the utility of the QTLs of the present invention naturally extends to predicting resistance in any salmonid. Consequently, when the method is applied to a coho salmon, reference is made to the coho salmon QTL (ie that located in linkage group 21 within the coho salmon genome, or in the chromosome of coho salmon that corresponds to that linkage group). However, when the method is applied to another species of salmonid, it is a QTL that corresponds to that located in linkage group 21 within the coho salmon genome, or in the chromosome of coho salmon that corresponds to that linkage group, that is referred to in the method.

As would be understood by the skilled person, a QTL that corresponds to the QTL of the present invention is an ortholog of the coho salmon QTL and provided in the species of salmonid to which the method is applied (ie the subject of the method). Establishing the corresponding QTL in which the polymorphisms of the present invention are found in any given salmonid is well within the ordinary abilities of the person skilled in the art, given the teachings provided herein for coho salmon. From a known domain in any given animal, one can identify corresponding domains in other animals. One can, for example, carry out multiple alignment analysis of nucleic acids encoding for the known QTL (using, for example, Clustal Omega analysis).

The inventors have found that the DNA polymorphisms of the present invention can be present in either of two forms, i.e. the DNA polymorphisms have two alleles. One allele can be characterized as being predictive of resistance to *Piscirickettsia salmonis* infection (i.e. the resistance allele); the other being predictive of non-resistance to *Piscirickettsia salmonis* infection. Salmonids are diploid organisms, and as such possess two copies of the polymorphisms (one copy to be found in each set of chromosomes). The step of determining the alleles in the first aspect of the present invention therefore may include the step of analyzing the DNA polymorphism provided in each set of chromosomes in order to determine whether each copy of the DNA polymorphism present is a resistance allele or is a non-resistance allele. When a salmonid subjected to the method of the present invention is determined to have two copies of the resistance allele for the DNA polymorphism (i.e. the salmonid is homozygous for the resistance allele), the salmonid is predicted to have resistance to *Piscirickettsia salmonis* infection. Conversely, when a salmonid subjected to the method of the present invention is determined to have two copies of the non-resistance allele for the DNA polymorphism (i.e. is homozygous for the non-resistance allele) the salmonid is predicted not to have resistance to *Piscirickettsia salmonis* infection, while the heterozygote is intermediate. It may be concluded that a salmonid that is predicted by the method to have *Piscirickettsia salmonis* resistance has a greater than normal probability of surviving exposure to *Piscirickettsia salmonis*. Conversely, it may be concluded that a salmonid that is predicted not to have *Piscirickettsia salmonis* resistance has a lower than normal probability of surviving exposure to *Piscirickettsia salmonis*.

The DNA polymorphism in question can be any one or more DNA polymorphism found in the QTL region of the present invention for the salmonid that is the subject of the method and that provide the above discussed predictive ability with respect to *Piscirickettsia salmonis* resistance. For example, in coho salmon the DNA polymorphisms of the invention have been mapped to linkage group 21 of the published coho genome reference (GenBank identifier NC_034194.1) or to one of two a standalone scaffold (GenBank identifier NW_018086972.1 and NW_018107982.1) within that genome reference. The published genome reference is a draft sequence, meaning that in future versions of the genome reference, the standalone scaffolds may end up merged to linkage group 21. Based on the Inventor's research, the scaffolds corresponding to NW_018086972.1 and NW_018107982.1 do in fact correspond to the same physical chromosome as does NC_034194.1. Consequently, the one or more polymorphism of the present invention may be provided in linkage group 21.

Examples of polymorphisms identified by the applicant in coho salmon, within linkage group 21 and that have a strong correlation with the resistance phenotype are provided in Table 3. Consequently, the polymorphisms of the present invention may be any one or more provided in Table 3. For example, the polymorphisms of the present invention may be any one or any combination of AX-169575201, AX-169638230, AX-169658111, AX-169600905, AX-169538214, AX-169531903, AX-169525869, AX-169664625, AX-169624356, AX-169638609, AX-169679883, AX-169598899, AX-169663696, AX-169631492. The polymorphism of the present invention may therefore be AX-169575201.

When the salmonid is not a coho salmon, the polymorphisms may be polymorphisms that correspond to any one or more of those provided in Table 3. As would be understood by the skilled person, a polymorphism that corresponds to a polymorphism provided in Table 3 is an ortholog of the polymorphism to which it corresponds. Establishing the corresponding polymorphism of the present invention in any given salmonid is well within the ordinary abilities of the person skilled in the art, given the teachings provided herein for coho salmon. From a known domain in any given animal, one can identify corresponding domains in other animals. One can, for example, carry out multiple alignment analysis of nucleic acids encoding for the known polymorphisms (using, for example, Clustal Omega analysis). Consequently, for example, when the salmonid is a rainbow trout, the polymorphisms may be any one or combination of those provided in Table 4.

The polymorphisms are chosen by their ability to predict resistance to SRS, and are all likely in linkage disequilibrium (LD) with a common causative mutation. The latter DNA polymorphism may be a single nucleotide polymorphism (SNP), a multiple nucleotide polymorphism, an addition mutation, or a deletion mutation. Each type of DNA polymorphism provided above is contemplated individually as part of the present invention for the step of determining in the methods of the present invention.

When the method is employed with two DNA polymorphisms, the two DNA polymorphisms could constitute one unit, hereafter referred to as a haplotype. Each haplotype can have four different alleles, corresponding to the four different combinations of DNA polymorphism alleles at the individual DNA polymorphisms (for example, if the haplotype is made up of one DNA polymorphism with alleles A and T, and one DNA polymorphisms with alleles T and G, the four possible haplotype alleles are A-T, A-G, T-T, and T-G. Each of these four alleles would be either a resistance allele or a non-resistance allele, in a manner analogous to the single DNA polymorphism method laid out above. Thus, in the hypothetical case of a haplotype having the four alleles A-T, A-G, T-T, and T-G, it could be that all A-T, A-G, and T-T were resistance alleles, whereas T-G was a non-resistance allele. In that case, an animal having one copy of the A-T allele and one copy of the A-G allele would be resistant to SRS, an animal having one copy of A-T and one copy of T-G would be semi-resistant, while an animal having two copies of T-G would be non-resistant. The terms "haplotype", "haplotype allele" and "DNA polymorphism allele" take their normal meanings as would be well understood by the skilled person in the art. However, for the avoidance of doubt, "DNA polymorphism allele" may mean one of two different nucleotide sequences at the site of a DNA polymorphism of the present invention (one allele being the "resistant allele", the other being the "non-resistant allele"). By "haplotype" means a set of closely linked DNA polymorphism (located close to each other on one and the same chromosome) that are for the most part inherited as a block (i.e. without recombination) from parents to offspring. By "haplotype allele" is meant a combination of alleles from the DNA polymorphisms constituting a haplotype, such as would be found on a single chromosome copy within a diploid animal. For example, the two polymorphisms may be any two selected from table 3. Alternatively, the one of the two polymorphisms may be selected from table 3 and one from table 4. Alternatively, the polymorphisms may be one selected from Table 3 and one selected form Table 7. For example, the polymorphisms may be those of Table 7, ie AX-169631492 and AX-169660070. The haplotype which has a cytosine base (C) at AX-169631492 and an adenine (A) base at AX-169660070 would be associated with the resistance (R) allele. Of the other three haplotypes AX-169631492-C+AX-169660070-C, and AX-169631492-A+AX-169660070-A would be considered to relate to an animal that is semi-resistant. Whilst, AX-169631492-A+AX-169660070-C is considered to relate to an animal that is non-resistant.

When the method is employed with three or more DNA polymorphisms, the three or more DNA polymorphisms could constitute a haplotype in a manner analogous to the situation described for two DNA polymorphisms. The three or more DNA polymorphisms can all be selected from any of those provided in table 3. Alternatively, one or more can be selected from table 3 and one or more selected from table 4. Alternatively, one from Table 3 and the two of Table 7.

The method may be applied to any salmonid, i.e., to any species within the family of Salmonidae family. Examples of such species are Atlantic salmon (i.e. Salmo salar), rainbow trout (i.e. *Oncorhynchus mykiss*), and coho salmon (i.e. *Oncorhynchus kisutch*). The salmonid may therefore be coho salmon or Atlantic salmon. The salmonid may be coho salmon.

The step of determining the presence or absence in a salmonid may be practiced on a sample taken from the salmonid. The sample may be any sample in which analysis of nucleic acid material is possible, as would be readily understood by the person skilled in the art. For the avoidance of doubt, the sample may be a skeletal muscle tissue sample, blood sample, liver sample, heart sample and/or a fin clip.

The skilled person would be well aware of all available methods capable of testing for the presence or absence of DNA polymorphism alleles, i.e. for the genotyping of a DNA polymorphism in an individual salmon (or another organism). For example, the method may involve sequence analysis of the salmon to be tested. Alternatively, the method may involve single base extension of DNA fragments terminating at the polymorphic site (e.g. iPLEX assays from Sequenom and Infinium assays from Illumina), allele-specific PCR (e.g. SNPtype assays from Fluidigm or KASPar assays from KBiosciences), competitive hybridisation of probes complementary to the different alleles (e.g. the TaqMan assay from Applied Biosystems), or genotyping-by-sequencing, i.e. deduction of genotypes from next-generation sequencing data (such as Illumina HiSeq data).

Consequently, in a further aspect of the present invention, there is provided a hybridization probe that is specific for one or more of the aforementioned DNA polymorphisms. The probe may hybridize with a nucleic acid comprising the resistant allelic form of one of the polymorphisms described above, or compliment thereof, but does not hybridize under the same conditions (eg of temperature and/or buffer) with a nucleotide sequence comprising the non-resistant allelic form of that polymorphism, or compliment thereof. Alternatively, the probe may hybridize with a nucleic acid comprising the non-resistant allelic form of one of the polymorphisms described above, or compliment thereof, but does not hybridize under the same conditions (eg of temperature and/or buffer) with a nucleotide sequence comprising the resistant allelic form of that polymorphism, or compliment thereof.

In a further aspect of the present invention, there is provided a SNP detection panel, in which a plurality of probes described above are provided. For example, the SNP panel may comprise probes for AX-169575201, or corresponding polymorphisms thereof. The SNP detection panel may comprise all or any combination of the polymorphisms provided in table 3 and or 7 or corresponding polymorphisms thereof. The probes may be bound to a substrate.

Any one or more of the probes or SNP detection panels may be used in the methods of the first aspect of the present invention, eg in order to determining in the salmonid the alleles present at one or more DNA polymorphism.

In a further aspect of the present invention, there is provided a kit for determining the allele present at one or more DNA polymorphism described above in a sample taken from a salmonid, wherein a kit comprises a primer for PCR amplification specific for a region adjacent to the one or more of the aforementioned DNA polymorphisms.

In a further aspect of the present invention, there is a method of detecting, in a sample from a salmonid, the alleles present at a DNA polymorphism associated with resistance to *Piscirickettsia salmonis* infection in a salmonid, wherein the DNA polymorphism is any one or more DNA polymorphism of the present invention.

In a further aspect of the present invention, there is provided a method for obtaining an indication of risk of a salmonid developing *Piscirickettsia salmonis* infection, the method comprising:
a. detecting, in a sample from the salmonid, the alleles present at a DNA polymorphism associated with resistance to *Piscirickettsia salmonis* infection, wherein the DNA polymorphism is any one or more DNA polymorphisms of any of the preceding claims, wherein the presence of the DNA polymorphism is indicative of the salmonid being resistant to *Piscirickettsia salmonis* infection.

In a further aspect of the present invention, there is provided a method of detecting one or more polymorphism at the QTL of any of the preceding claims, the method comprising: obtaining a sample from a salmonid; and assaying the sample to detect the one or more salmonid gene variants, the one or more salmonid gene variants selected from one or more of the DNA polymorphisms of any of the preceding claims.

In a further aspect of the present invention, there is provided a use of a DNA polymorphism associated with *Piscirickettsia salmonis* infection, wherein the DNA polymorphism is any one or more DNA polymorphisms of any of the preceding claims, for detecting salmonid being resistant to *Piscirickettsia salmonis* infection.

In a further aspect of the present invention, there is provided a method of producing offspring that have a higher than normal chance of having resistance to *Piscirickettsia salmonis* infection, the method comprising:
(a) detecting, in a sample from the salmonid, the alleles present at a DNA polymorphism associated with *Piscirickettsia salmonis* infection, wherein the DNA polymorphism is any one or more DNA polymorphism of any of the preceding claims, wherein the presence of the DNA polymorphism is indicative of the salmonid being resistant to *Piscirickettsia salmonis* infection; and
(b) using the salmonid being resistant to *Piscirickettsia salmonis* infection to produce offspring.

In a further aspect of the present invention, there is provided a method of detecting the allele present at one or more of the DNA polymorphisms discussed above which act as markers for a QTL in a salmonid, the method comprising: a. obtaining a sample from the salmonid; and b. detecting which allele of each of the one or more polymorphism is present in the sample. Step b. may include any methodology known to the skilled person capable of genotyping a polymorphism to determine allelic differences, examples of which are provided above. The method may therefore include the use of any one or combination of the probes, SNP detection panels or kits described above. The method may be for detecting the resistance allele of one or more of the polymorphisms of the first aspect of the present invention in a salmonid, the method comprising:—a. obtaining a sample from the salmonid; and b. detecting whether the allele is present in the sample by contacting the sample with an allelic specific hybridisation probe and detecting binding between the allele and the probe.

A salmonid that is predicted to have resistance to *Piscirickettsia salmonis* infection according to the present invention is more likely than normal to produce offspring that have a higher than normal chance of having resistance to *Piscirickettsia salmonis* infection. Consequently, in a further aspect of the present invention, there is provided a method of selecting a salmonid for use as broodstock, wherein the salmonid is selected based on the prediction by the method of the first aspect of the present invention that the salmonid will be resistant to *Piscirickettsia salmonis* infection.

In yet a further aspect of the present invention there is provided a method of breeding from a salmonid egg taken from a salmonid identified as being resistant to *Piscirickettsia salmonis* infection by the method of the first aspect of the present invention.

BRIEF DESCRIPTION OF THE DRAWINGS

Embodiments of the invention are further described hereinafter with reference to the accompanying drawings, in which.

DETAILED DESCRIPTION

Challenge Trial

Figure 1:
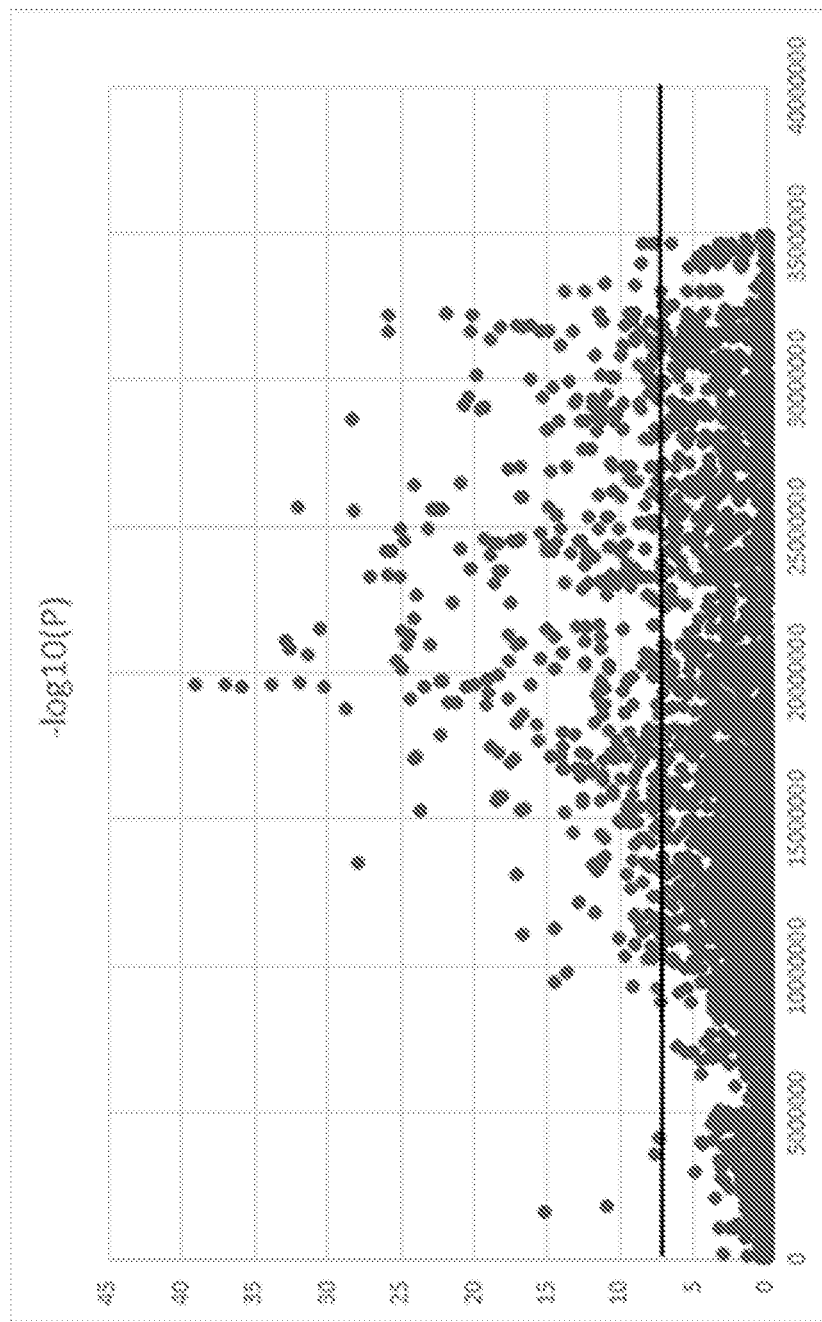
FIG. 1: Provides a graph showing the significance (−log 10(p-value)) of SNP loci with respect to SRS resistance by position at a sequence mapped to linkage group 21 (GenBank id: NC_034194.1) in Coho salmon. The values on the x-axis correspond to base numbers on the sequence. SNPs on or above the solid line are SNPs being experiment-wise significant based on Bonferroni correction. Only mapped SNPs of good genotype quality were included.

Survival data were obtained from a total of 2050 Coho salmon smolts belonging to 138 full-sibs families from the third yearclass of breeding nucleus of AquaGen Chile (yearclass 2014). All coho salmon in the breeding nucleus are the progeny of many generations of salmon farmed in Chile by AquaGen Chile. The original farmed salmon are derived from salmon originating in the USA. Each smolt was tagged with Passive Integrated Transponder (PIT) tags prior to testing. The challenge trial was conducted following a cohabitation model where 50% of the fish were injected intraperitoneally (IP) as shedders and the remaining 50% allocated together with these IP fish and left for infection by cohabitation (cohabitants or cohab). The test was performed at Fundacion Chile's Research Station (Puerto Montt, Chile). An average of 16 (ranging between 1 and 20) fish from each family were allocated in one tanks of 11 m3 and acclimatized for two weeks. During this period, salinity and water temperature was gradually increased reaching 100% seawater (32 ppm) and 14-15° C. IP fish (8 fish per family) were then anesthetized with benzocaine and infected by intra-peritoneal injection with 0.1 ml of *P. salmonis* (strain PM-18856, isolated from Rainbow trout). During the challenge, experimental fish were observed daily and mortality per family group was recorded daily for 63 days' post-infection (DPI). Body weight was recorded at the time of death for every dead fish or at the end of the challenge for survivors. Necropsy examination was performed on each dead fish and molecular diagnostic in a sample of dead fish was carried out in order to confirm *P. salmonis* and discard other pathogens as the cause of death. The molecular diagnostics involved qRT-PCR in a sample of dead fish in order to confirm *P. salmonis* and discard other pathogens as the cause of death. For RT-PCR amplifications the LigthCycler® 480 RNA Master Hydrolysis Probe Kit (Roche) was used in the LightCycler® 480 II thermal cycler. All RT-PCRs were performed using taqman Probe chemistry. Fin samples were taken from all fish and preserved in ethanol at −20° C. until DNA extraction. DNA extraction was performed in the Laboratory ADL Diagnostic Chile and then sent to the Centre for Integrative Genetics (Cigene), which is part of The Norwegian University of Life Sciences, for subsequent genotyping.

In the fifthyearclass (yearclass 2016) a new group of 2879 Coho salmon smolts belonging to 242 families were challenge against SRS. The challenge trial was conducted following the same model described above (cohabitation model), however due to the greater number of fish the challenge was performed in two tanks of 11 m³. An average of 6 (ranging between 4 and 7) fish from each family were allocated in each tank. During the challenge, experimental fish were observed daily and mortality per family group was recorded daily for 79 days' post-infection (DPI).

Genotyping

All fish from the test were genotyped (except for a few that were omitted due to poor DNA quality); 2025 individuals in total. Of these, there were 1042 fish in the IP group and 983 fish in the cohabitation group. In total, 138 full-sib families were present in the data. Individual coho salmon were genotyped using a custom Axiom array from Affymetrix (San Diego, CA, USA), proprietary to AquaGen. The SNP-chip contained 220,000 SNPs distributed across the coho genome.

Genotyping was done according to the Axiom 2.0 Assay Manual Workflow User Guide (http://media.affymetrix.com/support/downloads/manuals/axiom_2_assay_manual_workflo w_prepguide.pdf). Genotype calling was done using the Affymetrix Power Tools programs (http://www.affymetrix.com/estore/partners_programs/programs/developer/tools/powertool s.affx), according to "best practices" recommendations from Affymetrix (http://media.affymetrix.com/support/downloads/manuals/axiom_best_practice_supplemen t_user_guide.pdf).

The genetic material from the fifth yearclass (yearclass 2016) were genotyped following the procedure laid out above, except that only a subset of 72,016 of the 220,000 SNPs were genotyped, using a second SNP-chip (being a derivate of the original SNP-chip).

Statistical Analysis:

Survival at the end of test was used as phenotype. Initially, a linear model for survival at the end of the challenge test was fitted (not including any SNP effects). The model treated survival under IP and COHAB as potentially different genetic traits. The model (Model 0) was defined as follows:

$$\begin{bmatrix} y_1 \\ y_2 \end{bmatrix} = \begin{bmatrix} X_1 & 0 \\ 0 & X_2 \end{bmatrix} \begin{bmatrix} b_1 \\ b_2 \end{bmatrix} + \begin{bmatrix} Z_1 & 0 \\ 0 & Z_2 \end{bmatrix} \begin{bmatrix} a_1 \\ a_2 \end{bmatrix} + \begin{bmatrix} e_1 \\ e_2 \end{bmatrix}$$

where $$\begin{bmatrix} y_1 \\ y_2 \end{bmatrix}$$

is a vector of phenotypes for the two traits (survival at end of test for IP and COHAB, respectively), $$\begin{bmatrix} b_1 \\ b_2 \end{bmatrix}$$

is a vector of fixed effect for the two traits (trait by strain effects), $$\begin{bmatrix} a_1 \\ a_2 \end{bmatrix} \sim N(0, G \otimes A)$$

is a vector of random additive genetic effects for the two traits, $$G = \begin{bmatrix} \sigma_{a1}^2 & \sigma_{a1,a2} \\ \sigma_{a1,a2} & \sigma_{a2}^2 \end{bmatrix}$$

being the additive genetic (co)variance matrix, A is the numerator relationship matrix, and $$\begin{bmatrix} e_1 \\ e_2 \end{bmatrix} \sim N\left(0, \begin{bmatrix} I\sigma_{e1}^2 & 0 \\ 0 & I\sigma_{e2}^2 \end{bmatrix}\right)$$

is a vector of random residuals for the two traits. The model was analyzed using the ASREML software package (Gilmour, A. R., B. J. Gogel, B. R. Cullis and R. Thompson, 2009 ASReml user guide release 3.0, pp. VSN International Ltd., Hemel Hempstead.). The estimated heritabilities and the genetic correlation are presented in Table 1 below.

TABLE 1

Results from genetic analysis of SRS survival in Coho salmon. Heritabilities are given on the diagonal and genetic correlation above the diagonal

| Item | IP | COHAB |
|---|---|---|
| IP | 0.38 ± 0.07 | 0.91 ± 0.09 |
| COHAB |  | 0.37 ± 0.07 |

As seen above, the heritability for SRS resistance, measured as survival at end of test, is high (~0.4) and similar for IP and COHAB, even when measured on the observed scale. Furthermore, the genetic correlation between the two traits is close to unity (~0.9), indicating that genetic resistance is largely the same genetic trait under IP and COHAB.

The GWAS was performed by comparing log of restricted maximum likelihood (REML) values of the model above to the log REML values of Model 1 (below), assuming an effect of locus i in the model:

$$\begin{bmatrix} y_1 \\ y_2 \end{bmatrix} = \begin{bmatrix} X_1 & 0 \\ 0 & X_2 \end{bmatrix} \begin{bmatrix} b_1 \\ b_2 \end{bmatrix} + \begin{bmatrix} Z_1 & 0 \\ 0 & Z_2 \end{bmatrix} \begin{bmatrix} a_1 \\ a_2 \end{bmatrix} + \begin{bmatrix} m_{i1}\gamma_{i1} \\ m_{i2}\gamma_{i2} \end{bmatrix} + \begin{bmatrix} e_1 \\ e_2 \end{bmatrix}$$

where $m_{i1}$ and $m_{i2}$ are vectors of genotypes (coded as 0, 1 or 2, for homozygotes, heterozygotes and the other homozygote) at locus i, of IP and cohabitation fish, respectively, while $\gamma_{i1}$ and $\gamma_{i2}$ are the allele substitution effects for the two traits at the same locus. Hence, independent locus effects were fitted for IP and COHAB. The REML values are only comparable given that the same fixed effects are fitted in both models, and the allele substitution effects where thus defined as random:

$$\begin{bmatrix} \gamma_{i1} \\ \gamma_{i2} \end{bmatrix} \sim N\left(0, \begin{bmatrix} \sigma_{\gamma 1}^2 & 0 \\ 0 & \sigma_{\gamma 2}^2 \end{bmatrix}\right)$$

Animals with missing genotype at the given locus were removed from both models. The two models were then compared using likelihood ratio test statistics:

$$D = 2(lnL_1 - lnL_0) \sim \chi_2^2$$

where $lnL_0$ and $lnL_1$ are the natural logarithms of the REML likelihoods of Model 0 and 1, respectively. Significance was tested using a Chi-square test with two degrees of freedom (as two additional variance components were included in Model 1). The effect of each locus was tested separately one at a time, i.e., 220 k tests were performed, implying that correction for multiple testing (Bonferroni correction) had to be performed to reduce the risk of false positives.

Results:

The GWAS revealed a highly significant SNP mapped to a single sequence (corresponding to chromosome 4 in Rainbow trout). In FIG. 1, the significance ($-10 \ln(P)$) of mapped SNPs of good quality plotted over sequence positions are shown.

Figure 2:
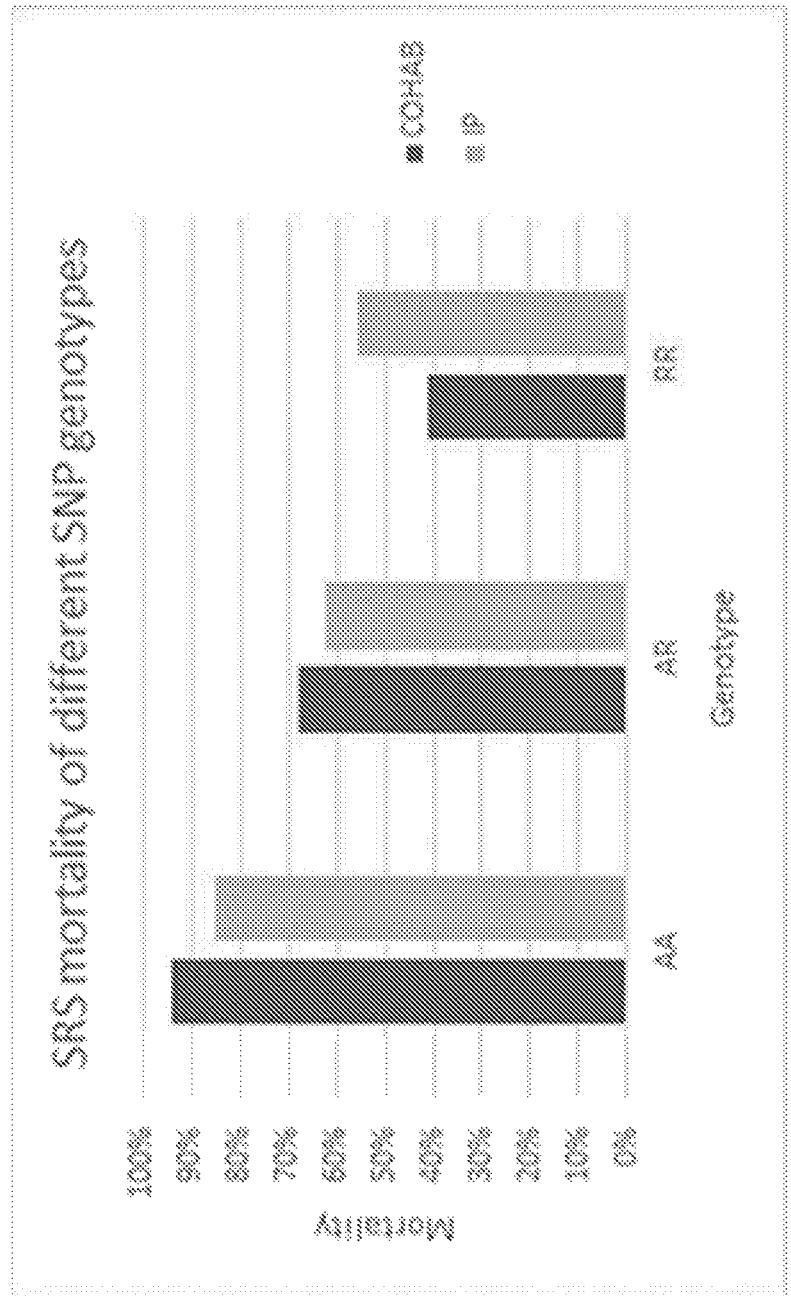
FIG. 2: Provides a graph showing average mortality in COHAB and IP challenged coho salmon for different genotypes of the most significant SNP locus. AA=homozygote susceptible, AR=heterozygote, RR=homozygote resistant.

As seen from FIG. 1, there are numerous SNPs that are highly significant. The QTL is located towards the end of the sequence (most significant around 50 Mb). Table 2 and FIG. 2 shows the mortality for the different genotypes at the single most significant locus.

TABLE 2

Number of fish and number of mortalities for each genotype of the single most significant SNP locus. Genotypes are given as AA (homozygote susceptible), AR (heterozygote) and RR (homozygote resistant)

| Challenge method | Genotype | N | Dead at end of test |
|---|---|---|---|
| COHAB | AA | 663 | 625 |
|  | AR | 269 | 183 |
|  | RR | 51 | 21 |
| IP | AA | 644 | 547 |
|  | AR | 330 | 206 |
|  | RR | 68 | 38 |

The most common genotype was the unfavourable homozygote (>50%, Table 2), giving ample room for improvement.

In a second step, a new GWAS was performed, where the single most significant locus in the analysis above were included as a fixed strain by locus interaction (strain-specific genotype effects, rather than regression on number of SNP alleles). This model was then compared against a model additionally including effects of other SNPs (as a regression). Again, several loci on the same sequences turned up as significant.

All the listed significant SNPs were additionally mapped to three sequences (NC_034194.1, NW_018086972.1, and NW_018107982.1). The regions within these sequences harbouring the listed significant QTLs were found to be orthologous to one and the same chromosome in rainbow trout. The results thus point towards a single highly significant QTL affecting SRS resistance in coho. The single most significant locus explains, respectively, 16% and 46% of the genetic variation in SRS resistance under IP and COHAB infection (more if additional SNPs around this position are included).

Later, the material from the second challenge test (year class 2016) was tested in a confirmatory GWAS. In this GWAS, the statistical analysis was conducted as laid out above, except that a common allele substitution effect was assumed for IP-injected fish and cohabitants. The results from this GWAS confirmed the ability of the SNPs in Table 3 to predict resistance to SRS, in the sense that all SNPs had large and positive allele substitution effects at the resistance allele (Table 6).

A haplotype-based approach was employed in order to identify combinations of SNPs which, when combined into a haplotype, might prove superior for determining resistance to SRS. The approach assumed that the diagnostic behaviour of haplotypes was due to a single causative mutation, with two alleles, being located in the vicinity of the haplotypes. The following approach was followed, individually on the two data sets (year class 2014 and year class 2016): First the genotypes were phased using the software Fimpute. Next, a region of coho linkage group 21 was singled out, centred on the diagnostic SNPs already identified; this region stretched from position 14,893,760 to 34,893,760 within the sequence of NC_034194.1. Each SNPs within this region was next combined with every SNP located not more than 10,000 base pairs away from itself. Then, for every pair of SNPs, this procedure was followed: 1) two-SNP haplotypes were extracted from each animal belonging to the data set, 2) for every possible assignment of Q or q (the two alleles at the underlying causative mutation) to each of the four possible haplotype alleles, two-SNP haplotypes were translated to alleles at the underlying QTL, 3) given these causative-mutation genotypes, a Genome-Wide Association Study was carried out, following the procedure laid out above. This method identified two-SNP combinations with high diagnostic power, as well as the haplotypes (within each combinations) linked to the high-resistance allele at the underlying causative mutation.

One combination of SNPs was found to be particularly diagnostic (Table 7). The two SNPs were AX-169631492 and AX-169660070. This SNP combination was the most significant one in year class 2014 as well as in year class 2016. The p-value of test for association between the haplotype and SRS survival was 3.04995E-44 and 6.15085e-22, respectively, in the two-year classes. The combination of SNPs can be used in order to predict resistance to SRS, in the following manner: Broodstock candidates can be genotyped for the two SNPs. Genotypes at the two SNPs can next be transformed into haplotypes, using the software Phase or similar software. Finally, haplotypes can be transformed into alleles at the underlying, causative locus. This transformation goes as follows: the haplotype which has a cytosine base (C) at AX-169631492 and an adenine (A) base at AX-169660070 (which we may denote as AX-169631492-C+AX-169660070-A) is associated with the resistance (R) allele at the underlying causative mutation. The other three haplotypes (AX-169631492-C+AX-169660070-C, AX-169631492-A+AX-169660070-C, and AX-169631492-A+AX-169660070-A) are all associated with the non-resistance allele (A, for Affected) or semi-resistance allele at the underlying causative mutation. An animal which is, in this way, found to have two copies of the R allele at the underlying causative mutation will have particularly high resistance to SRS.

TABLE 3

Allele substitution effects and significance levels of SNPs associated to SRS resistance in coho salmon

| SNP identification | Sequence identifier (GenBank) | Position in sequence | Allele subst. eff. (IP), percent-age survival | All. subst. eff. (COHAB), percent-age survival | Frequency resistant allele (%) | Mutation | Resistant allele | $\chi^2$ | P |
|---|---|---|---|---|---|---|---|---|---|
| AX-169575201 | NW_018086972.1 | 3487 | 19 | 27 | 21 | A (SEQ ID NO: 34)/ G (SEQ ID NO: 20) | G (SEQ ID NO: 20) | 203.39 | 6.83E−45 |
| AX-169638230 | NC_034194.1 | 19566002 | 20 | 25 | 21 | T (SEQ ID NO: 35)/ G (SEQ ID NO: 21) | G (SEQ ID NO: 21) | 174.29 | 1.42E−38 |
| AX-169658111 | NC_034194.1 | 19572302 | 19 | 25 | 20 | A (SEQ ID NO: 22)/ C (SEQ ID NO: 36) | A (SEQ ID NO: 22) | 164.726 | 1.70E−36 |
| AX-169600905 | NC_034194.1 | 19538254 | 18 | 23 | 23 | A (SEQ ID NO: 23)/ C (SEQ ID NO: 37) | A (SEQ ID NO: 23) | 160.118 | 1.70E−35 |
| AX-169538214 | NC_034194.1 | 19564847 | 18 | 23 | 22 | A (SEQ ID NO: 38)/ C (SEQ ID NO: 24) | C (SEQ ID NO: 24) | 150.764 | 1.83E−33 |
| AX-169531903 | NC_034194.1 | 20840210 | 18 | 22 | 24 | A (SEQ ID NO: 39)/ G (SEQ ID NO: 25) | G (SEQ ID NO: 25) | 144.69 | 3.81E−32 |
| AX-169525869 | NC_034194.1 | 25645326 | 18 | 22 | 24 | A (SEQ ID NO: 26)/ C (SEQ ID NO: 40) | A (SEQ ID NO: 26) | 142.606 | 1.08E−31 |
| AX-169664625 | NC_034194.1 | 19656167 | 19 | 20 | 24 | T (SEQ ID NO: 41)/ C (SEQ ID NO: 27) | C (SEQ ID NO: 27) | 141.95 | 1.50E−31 |
| AX-169624356 | NC_034194.1 | 20604653 | 18 | 20 | 26 | T (SEQ ID NO: 28)/ C (SEQ ID NO: 42) | T (SEQ ID NO: 28) | 139.086 | 6.28E−31 |
| AX-169638609 | NC_034194.1 | 21523060 | 15 | 19 | 32 | A (SEQ ID NO: 29)/ C (SEQ ID NO: 43) | A (SEQ ID NO: 29) | 135.756 | 3.32E−30 |
| AX-169679883 | NC_034194.1 | 19556219 | 17 | 22 | 22 | A (SEQ ID NO: 44)/ G (SEQ ID NO: 30) | G (SEQ ID NO: 30) | 134.312 | 6.83E−30 |
| AX-169598899 | NC_034194.1 | 18790854 | 16 | 20 | 24 | A (SEQ ID NO: 31)/ C (SEQ ID NO: 45) | A (SEQ ID NO: 31) | 127.35 | 2.22E−28 |
| AX-169663696 | NC_034194.1 | 23303080 | 16 | 21 | 23 | T (SEQ ID NO: 32)/ G (SEQ ID NO: 46) | T (SEQ ID NO: 32) | 119.948 | 8.99E−27 |
| AX-169631492 | NC_034194.1 | 20989871 | 7 | 10 | 67 | A (SEQ ID NO: 47)/ C (SEQ ID NO: 33) | C (SEQ ID NO: 33) | 28.584 | 6.21E−7 |

Table 4: The most significant high-quality SNPs fitted in addition to the top SNP in Table 3, and mapped to same sequence corresponding to chromosome 4 in Rainbow trout.

TABLE 4

The most significant high-quality SNPs fitted in addition to the top SNP in Table 3, and mapped to same sequence corresponding to chromosome 4 in Rainbow trout.

| SNP-ID | Sequence identifier (GenBank) | Position in sequence | $X^2$ | P | Mutation |
|---|---|---|---|---|---|
| AX-169530318 | NC_034194.1 | 24909062 | 36.06 | 1.48E−8 | T/C |
| AX-169538288 | NC_034194.1 | 24359203 | 30.99 | 1.87E−7 | A/C |
| AX-169538314 | NW_018086972.1 | 61338 | 24.98 | 3.76E−6 | T/C |
| AX-169628414 | NW_018086972.1 | 56659 | 24.98 | 3.76E−6 | T/G |
| AX-169618068 | NC_034194.1 | 30045670 | 24.36 | 5.13E−6 | A/G |

TABLE 5

Nucleotide sequences association with SNP polymorphisms included in the application

| SNP-ID | Nucleotide sequence containing polymorphism | Genebank id | Position |
|---|---|---|---|
| AX-169575201 | ATCATTCAGAATATATCCTCAAACCCAGATATGTCAAACCATCAA CACTTTCAAGCATTGTTCCATTACTTGCATGGATTTTGAAATGGC CAGCTGTGGA[A/G]TTTATTCTTTTCTGTGTACATATCCATGCA ATGTTGTCTTAATGTGTGTGTGTATATATATCAGAGCGAGGAG AAGACCCGTATTAACTCATCCTTGG (SEQ ID NO: 1) | NW_018086972.1 | 3487 |
| AX-169638230 | AATGCTTTATTTTTACTTTGCAATATGCAGTATTCAGTCCACTGA GAGAGGTACAGGACATAACAATAGCCCAAAACAAAATGAACAAGA TTGAGTTTTT[T/G]GGCCTTCTACAATGGCTGAACCTGTCACAC AATCTTATAGGGGAAATCTATTCTTACACATTTGAAAATCTACCC AGTATTTTAGAACTAGACTTATCTT (SEQ ID NO: 2) | NC_034194.1 | 19566002 |

TABLE 5-continued

Nucleotide sequences association with SNP polymorphisms included in the application

| SNP-ID | Nucleotide sequence containing polymorphism | Genebank id | Position |
|---|---|---|---|
| AX-169658111 | GTAATTAGAAATCTGTATGCCGTGCTGTAGTGAGTCATACTGCCT GCAGAGCCCGGTCTAATGTATATGTTTGCTCTGTAGCAGAAGGTT TGGCCAGGAT[A/C]TTGGACCACCAGGGAAACCTGTTAGAAGGG GGGATGGATGGCAGGAGCCAGAAGAGCAAATAAAACACAGGATTC GTGAATGAATGGAATTCGTAAATGA (SEQ ID NO: 3) | NC_034194.1 | 19572302 |
| AX-169600905 | TGGTGGTTCTGGAGGCTGCTGCCTTTATTTTATGAGGGATCTGAG GAGTCTCCTCTACATGAGGCCTCAGGTGATCCATGCTTATTTTAG GGAAGATAAC[A/C]CCCTTGTCATCTTCCACGTCCACACTTTTG CTTTTGAGACCTCGAATCGTACATTGGCCGAGATAGTTGTGATCT AGTTCGCCCCCTTTCCTCTGCTGGT (SEQ ID NO: 4) | NC_034194.1 | 19538254 |
| AX-169538214 | TCTCTTGTGACACCTGACTAGAGTAAGGCTGTGTACCCAGCACAC AAATAAAGTCTTTTCATTATCAGATTGGGACAGAAACTGTGAACT ATGGATATTT[A/C]AAAGAGACAGTTAAATGTGAATTCGCTATA GCCAAGGATGTCTCATCTGAAGCGGATACTCTTAAGACTGATACA GCCAACAAATTAATTTATGGACTGT (SEQ ID NO: 5) | NC_034194.1 | 19564847 |
| AX-169531903 | GACCTCCTCTGGTTTCTCTAGAACCGCCCATGAATGCTGCTTATC CTCTGGTCCACATTCCTCTGTGATGTCATTATAAAATCCCACAAA CTTCTTGTTG[A/G]TGGAATCTTCGAGGAAAACGTCATTGACAT CATCTCCAGACCTGATATGCTCTAAAACCCTGTTGACAGAGTTCT GTGCGTCGGCCCAGGAATGTAGCCT (SEQ ID NO 6) | NC_034194.1 | 20840210 |
| AX-169525869 | TCGCTCACGTTCTCCAAGTTGATGACGTTCCAGATGGCTTTGACG TAGTCGGGTCGAACGTTCTTGTACTGGCGATAGTAGATGTTCCCA TATATCAATA[A/C]CCAGCAGAGGGACCAAACCTGGGGAGAAAA AAATGACTTTAAGTAAAATAATGATGCAGCTTCAAAGTATTTGAA CAGGCCAGACATCCATATGGTTATT (SEQ ID NO: 7) | NC_034194.1 | 25645326 |
| AX-169664625 | AACTGAACAGGATCAGTTGGATCTGACAAAAAGCCATTCAACTTT GATAGATGGCAAAGGAGTATTTCAGTGTCTACAAACTGTAAGGTC TGAAGAACAC[T/C]GGCTTAGGGGAAGCCCTTTCAGCCCGGTAT CTGTCTCTACTGATCCAAATGAAATGGAGTTGACCAGGTGCCCAA CTTTTGCCATTGACTTCAAAGCCAT (SEQ ID NO: 8) | NC_034194.1 | 19656167 |
| AX-169624356 | AAGATCTCTGCAAAAACGGCACAATTAATCACATATTTCTTGAGT TACTTTTGTGTATATACTGGCTACAGCATCTCAAAATAGACAGAC AGTACTATTG[T/C]CGCTTTTTTCTCATTTTGTCACGACTTCGG CCGAAGTTGGCTCCCCTGCCTGTTCGGGCGGTGCTCGGCAGTCGT CGTCACCGTCCTACTAGCCGCCGTC (SEQ ID NO: 9) | NC_034194.1 | 20604653 |
| AX-169638609 | TCAGAGGTTAGCTTATCATTACTTTCCCTTGGTGCCTTGCGGTTA CATCGTTTTGTACCGTGTTCAGTCATCAATAATACAGTTTCTAAT CCGGTTACAG[A/C]CAGGAGAGCCTTCTGCATTATAATAGCGTA CAGTAATCTCCATCCATTGACACTGTAGCCCATCCTCATACCTGT CAATGATGAGCCATTGGGTTCTGAG (SEQ ID NO: 10) | NC_034194.1 | 21523060 |
| AX-169679883 | GTTGATTCAACCTCAACACATATTTGGGGTTGAAATGAGATGGAA ACAATGTTGATTCACCCAGCTGTTACCCAGTGGCTGGTTGTTTAG CATGATAGGC[A/G]GGTTCAGAGAGAACTTGTTTGTTCTTGGTC AGCAACTACGCCATCCAGAAAGGAACTTCCTTCCTTGATCAATCG AAGACATGGAGGGAGGCTTATATAA (SEQ ID NO: 11) | NC_034194.1 | 19556219 |
| AX-169598899 | TAAATAAAACATGTATATGCTTTACAATTTACTACAAATCCAGAA AGTATGGTGTCATAGTATTTTCCATGCATACATTATGCTGCTGTC ATGAACAATT[A/C]ATCTAATTAAACATGAGTTAATATTTGTTG TAGTAAAAAAGTATATCTCCCACAGATTAAAACATCATTTCCTCC ATTTTGTCCGGCGCTGGTAGACGTC (SEQ ID NO: 12) | NC_034194.1 | 18790854 |
| AX-169663696 | TTAGATCTAAAGTCGACCACACTTACCGCTGTGTCCCTATGTAGG CTGCAGTGACATGTATTCATGGATGCCAAGGAAAGCCATGCTTCC ACCCAAAAAT[T/G]ACGAATAAAAATGTAACAAATTTAAAAACA TATCTTTCGTCTCACTGCGTTTCATAATTTCCCTTCAATTCGCAA GAGGCTGAATGTATCTCACCAGTGA (SEQ ID NO: 13) | NC_034194.1 | 23303080 |
| AX-169530318 | GACGTGCAGATCCCTGGACGATGGCGTACAGTAAGAACACCAAGA GGAAGTTTTTCTTCAACAAGATGACTAAACAGTCCACTTACGACC TGCCAGCCAA[T/C]TCTGTGGCCCCGTTCCAGTGCGTACCACTA TGCACCGGTCTCAAATCTGTGTGGTAGACTAGGATATGCGACA AGGAATTGTCTGCATGTTTTTGCAT (SEQ ID NO: 14) | NC_034194.1 | 24909062 |

TABLE 5-continued

Nucleotide sequences association with SNP polymorphisms included in the application

| SNP-ID | Nucleotide sequence containing polymorphism | Genebank id | Position |
|---|---|---|---|
| AX-169538288 | TAGATGCCTCCTGCAGAGTCAACTACACATCAAGATTGAGAAGTG GGAGTTCCATGTATCCCAAGTCTCTTTCCTGGGACACATGATCTC TACCGCCAGC[A/C]TTAAAATGGACCCTGTTAAGGTTAGGGCGG TCACTGACTGGCCCCGTCCCGCCTCACTTAAACAAGTCCAGCGGG TCCTCGGGTTTGCCAATTTTTACAG (SEQ ID NO: 15) | NC_034194.1 | 24359203 |
| AX-169538314 | AGGCCTAATGGTGGCCATTGGCTGGGGCTACGCTATCCCTCCCAA TGCCACAGCATTCCACAGCTACGGCCTCTGCAACACATCACACTT CTCAGACGTA[T/C]GTTCAGTGCTCTTTGACACTAGATTGAAGA AGGATGGTTGATTTTGATGACATTGTAGAGCAGATTGTTGTCAAA AAAGGAAAGCGCCAGCTTACTCTTT (SEQ ID NO: 16) | NW_018086972.1 | 61338 |
| AX-169628414 | GCTAGTTGTTTTTAGAGAACCAGCTGTGCTTATGGCTTAACACAA TTTAGTTTGCCGTGGAAAATATCAACGCCATGACAACATTCTCAT GGCCAAATCA[T/G]GGAAGCAGTAATATATCACACTAGCAAATA CCAGCGCCATACCGTGACCAAATACCATACCGTGATGGAGATAAT TATGAAACTAGCTAGCTTGTTAACT (SEQ ID NO: 17) | NW_018086972.1 | 56659 |
| AX-169618068 | GTAAGCATTTCATGGTAAAGTCTACACCCGTTGTATTTGGCGCAT GTGACAAATATTTTTGGGGGTATTTTATTTTATTCTCATGTATCA CGCTTGTGAC[A/G]TCCCTGGCCTTTTGCAGCACTGATGCTTCT GTAATGAGATGCTATATGAGACATGCCAAAGCACCCACACACTGT GACAAAGAGTAAAACAACATGAGAC (SEQ ID NO: 18) | NC_034194.1 | 30045670 |
| AX-169631492 | TTTATTTTTCACCGTACACAAGTCTTCAAATGGGT[A/C]ATTTC CCCCATGTATATTCATTAGTCTGCAGGTGT (SEQ ID NO: 19) | NC_034194.1 | 20989871 |

TABLE 6

P-values from test for association between SRS-resistance performed on year class 2016,

| SNP identification | P | Allele subst. eff., percentage survival | Resistance allele |
|---|---|---|---|
| AX-169575201 | 2.35E−05 | 13.3816 | G |
| AX-169638230 | 0.001482368 | 9.78213 | G |
| AX-169658111 | 0.003918699 | 9.1405 | A |
| AX-169600905 | 1.11E−10 | 17.042 | A |
| AX-169538214 | 0.001165712 | 9.91941 | C |
| AX-169531903 | 1.07E−11 | 16.572 | G |
| AX-169525869 | 2.82E−05 | 11.5417 | A |
| AX-169664625 | 0.000144424 | 11.5206 | C |
| AX-169624356 | 0.000621399 | 9.74517 | T |
| AX-169638609 | 0.000763262 | 7.95602 | A |
| AX-169679883 | 0.042218418 | 6.53488 | G |
| AX-169598899 | 0.103755968 | 4.37417 | A |
| AX-169663696 | 6.96E−08 | 19.8954 | T |

Table 7: Nucleotide sequences association with SNP polymorphisms, forming diagnostic haplotypes, which are included in the application

TABLE 7

Nucleotide sequences association with SNP polymorphisms, forming diagnostic haplotypes, which are included in the application

| SNP-ID | Nucleotide sequence containing polymorphism | Gene-bank id | Position | Resistance Allele |
|---|---|---|---|---|
| AX-169631492 | TTTATTTTTCACCGTACACAAGTCTT CAAATGGGT[A/C]ATTTCCCCCATG TATATTCATTAGTCTGCAGGTGT (SEQ ID NO: 19) | NC_034194.1 | 20989871 | C |
| AX-169660070 | CTGTTTATATCTATGGCCAGCTAGTC TTAATGGTT[A/C]GTGATGGAGTAA GACAGGTTCACATCTGGGAGGAT (SEQ ID NO: 48) | NC_034194.1 | 20989315 | A |

Features, integers, characteristics, polymorphisms or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A method of detecting one or more coho salmon gene variants, the method comprising:
obtaining a sample from a coho salmon;
assaying a nucleic acid of the coho salmon; and
detecting presence of a guanine at position 101 of SEQ ID NO:1 and/or an adenine at position 101 of SEQ ID NO:3.

2. The method of claim 1 further comprising: breeding the coho salmon.

3. A method of breeding coho salmon, said method comprising:
breeding a coho salmon which has a guanine at position 101 of SEQ ID NO:1 and/or an adenine at position 101 of SEQ ID NO:3, wherein a sample from the salmon has been tested to detect presence of guanine at position 101 of SEQ ID NO:1 and/or adenine at position 101 of SEQ ID NO:3.

* * * * *